United States Patent
Bodlaender et al.

(10) Patent No.: US 8,478,606 B2
(45) Date of Patent: Jul. 2, 2013

(54) ELECTRONIC AGENDA WITH WEIGHT MANAGEMENT FUNCTION

(75) Inventors: Maarten Peter Bodlaender, Eindhoven (NL); Arvid Randal Nicolaas, Eindhoven (NL); Olivier Schneider, Eindhoven (NL); Mariana Simons-Nikolova, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 289 days.

(21) Appl. No.: 12/158,052

(22) PCT Filed: Dec. 21, 2006

(86) PCT No.: PCT/IB2006/054992
§ 371 (c)(1), (2), (4) Date: Jun. 19, 2008

(87) PCT Pub. No.: WO2007/072452
PCT Pub. Date: Jun. 28, 2007

(65) Prior Publication Data
US 2008/0306775 A1    Dec. 11, 2008

(30) Foreign Application Priority Data
Dec. 23, 2005 (EP) .................................. 05112916

(51) Int. Cl.
*G06Q 10/00* (2012.01)
*G06Q 50/00* (2012.01)

(52) U.S. Cl.
USPC ................................................. 705/2; 705/3

(58) Field of Classification Search
USPC .......................................................... 705/2
See application file for complete search history.

(56) References Cited

U.S. PATENT DOCUMENTS

| 6,083,006 | A  | * | 7/2000 | Coffman ........................ 434/127 |
| 6,188,957 | B1 | * | 2/2001 | Bechtolsheim et al. ...... 701/209 |
| 2005/0004436 | A1 | | 1/2005 | Nissila et al. |
| 2005/0021371 | A1 | | 1/2005 | Basone et al. |
| 2005/0113650 | A1 | | 5/2005 | Pacione et al. |
| 2005/0121504 | A1 | | 6/2005 | Sanders et al. |

FOREIGN PATENT DOCUMENTS

| EP | 1473655 | 11/2004 |
| WO | WO0075748 | 12/2000 |
| WO | WO0232037 | 4/2002 |
| WO | WO2004107227 | 12/2004 |
| WO | WO2005029242 | 3/2005 |

OTHER PUBLICATIONS

Oja, Daily walking and cycling to work: their utility as health-enhancing physical activity, Education and Counseling, vol. 33, Supplement 1, Apr. 1, 1998, pp. S87-S94.*

* cited by examiner

*Primary Examiner* — Tran Nguyen

(57) ABSTRACT

A weight management system (10) comprising logging means (11) for logging past food intake events and past energy expenditure events, means for receiving (11) agenda entries and storage means (12) for storing the past food intake events, the past energy expenditure events and the agenda entries. The system further comprises a processor (13) for, based on the past food intake events, the past energy expenditure events and the agenda entries, scheduling at least one future food intake event or at least one future energy expenditure event and adding the future food intake event or the at least one future energy expenditure event to the storage means (12) as one of the agenda entries. An output (14) is provided for presenting the agenda entries to the user. The system (10) enables integrating a weight management system with a user's personal agenda.

15 Claims, 4 Drawing Sheets

ELECTRONIC AGENDA WITH WEIGHT MANAGEMENT FUNCTION

The invention relates to a weight management system comprising logging means for logging past food intake events and past energy expenditure events, storage means for storing the past food intake events and the past energy expenditure events, a processor for, based on the past food intake events and the past energy expenditure events, planning at least one future food intake event or at least one future energy expenditure event and an output for presenting the at least one future food intake event and/or the at least one future energy expenditure event.

The invention further relates to a travel planner, which may be used in the weight management system.

The invention further relates to a method for managing weight.

The invention further relates to a computer program product for performing said method.

Such a weight management system is, for example, known from European patent application EP1473655 A1. EP 1473655 A1 describes a method and a device for weight management of humans. The user's initial weight and target weight are received via a user interface, then food intake amount and exercise instructions to be represented via the user interface if the device are generated on the basis of the difference between the user's initial weight and his target weight. In addition, the actual user's energy expenditure, food intake amount and weight are received via the user interface. The food intake amount and/or exercise instructions are modified on the basis of the change in the user's weight. In an embodiment receives information defining the user's workload and takes the workload into account when generating his energy expenditure.

It is a problem of the system according to EP 1473655 A1, that people often have difficulties with following the exercise and food intake amount instructions. On busy days, people have little time for exercising and preparing healthy meals. By not following the instructions, the chance of realizing the target weight is considerably reduced. It is therefore an object of the invention to provide a weight management system, which provides instructions for a user, which are easier to be followed.

According to the invention this object is achieved by providing a system as described in the opening paragraph, which system further comprises means for receiving agenda entries, and wherein the agenda entries are stored in the storage means, and the processor is arranged to, based on the past food intake events, the past energy expenditure events and the agenda entries, schedule at least one future food intake event or at least one future energy expenditure event and to add the future food intake event or the at least one future energy expenditure event to the storage means as one of the agenda entries.

The system combines a user's normal agenda with a weight management system. When, future energy expenditure events and future food intake events are planned, the user's agenda entries are taken into account. As a result, the planned events will not conflict with a user's normal agenda and it will be much easier for the user to follow the suggestions of food intake events and energy expenditure events as planned by the weight management system.

In a preferred embodiment of the weight management system according to the invention, the logging of past food intake events comprises logging an amount of received metabolic energy, the logging of past energy expenditure events comprises logging an amount of expended metabolic energy, and the processor is operative to schedule the at least one future food intake event and the at least one future energy expenditure event in such a way as to balance a difference between the received and the expended metabolic energy according to a predetermined balancing criterion.

With 'received metabolic energy', all energy is denoted which can be used for the metabolic processes in an organism. Metabolic processes are all energy consuming processes in the cells of living organisms. The energy consumption on the cellular level leads to all biological and behavioral processes, like growing, breathing, walking, thinking, writing, etc. The 'received metabolic energy' will generally come from food and drinks. With 'expended metabolic energy', the energy used by the organism is denoted. Standard measures for metabolic energy are Joules or Calories. Eating a 100 grams candy bar may, for example, result in 483 Kcal of received metabolic energy. An half hour walk may, for example, result in 160 Kcal of expended metabolic energy.

The difference between the received and the expended metabolic energy indicates whether the user is likely to gain or lose weight. When a user wants to stabilize his/hers weight, the difference should be approximately zero. When a user wants to lose weight, slightly more metabolic energy should be expended than received. In this embodiment, the processor monitors the difference by adding all amounts of metabolic energy, received during the logged food intake events and subtracting all amounts of metabolic energy, expended during the logged energy expenditure events. Then, the processor schedules future events, for balancing the difference. Predetermined balancing criterions are used for performing the balancing. For example, the relative difference between intake and expenditure over a given period must be smaller than a predetermined maximum relative difference.

In a further embodiment of the weight management system according to the invention, two successive agenda entries comprise respective geographical locations and the processor is operative to generate a travel advice for traveling between the respective geographical locations of the successive agenda entries, the travel advice comprising at least one tip on a means of conveyance to be used.

This embodiment has the advantage that it provides for the possibility to integrate the planning of energy expenditure events with entries in a user's agenda. Some means of conveyance may be used for expending energy, while other means of conveyance may be used for fast traveling. When, for example, walking or cycling between two locations, the user expends significant amounts of energy. On a busy day, the weight management system may suggest walking and cycling between locations instead of planning separate physical exercise activities.

The tip on the means of conveyance to be used may be determined based on the distance between the respective geographical locations, on an amount of available time between the successive agenda entries and on an amount of metabolic energy needed for use of the means of conveyance.

When more time is available between two agenda entries, and the geographical locations are not far from each other, relatively slow, but energy demanding, means of conveyance, such as walking or cycling, may be suggested. When less time is available between two agenda entries and the geographical location are further away from each other, faster means of conveyance, such as trains or cars are suggested. When, for example, a user has two appointments at two different locations which are 4 miles apart from each other and the user has half an hour of time for traveling between these two locations, then he may be advised to go by bike. If, however, the time between the two appointments is only fifteen minutes, the use of a car, bus or taxi may be suggested. When a car or bus is used, the corresponding energy expenditure will be very low.

Alternatively or additionally, the tip on the means of conveyance to be used may be determined based on the past and/or future food intake events and the past and/or future energy expenditure events.

This allows for suggesting more energy demanding means of conveyance when the weight management system detects a period of (threatening) energy surplus and suggesting less energy demanding means of conveyance when the weight management system detects a period of (threatening) energy deficit. When, for example, the user has already performed several physical exercise activities in the last few days, the system may suggest taking the bus. When a dinner party is planned for the evening, the system may suggest using a bike instead.

According to another aspect of the invention a travel planner is provided, comprising a module for receiving food intake information and/or energy expenditure information and two geographical locations, and a module for generating a travel advice for traveling between the geographical locations, the travel advice comprising at least one tip on a means of conveyance to be used, wherein the tip on the means of conveyance to be used is determined based on the received food intake information and/or energy expenditure information, on the two geographical locations and on an amount of metabolic energy needed for use of the means of conveyance.

The travel planner may, e.g., be used in the weight management system according to the invention or may use output data of a conventional weight management system.

These and other aspects of the invention are apparent from and will be elucidated with reference to the embodiments described hereinafter.

BRIEF DESCRIPTION OF THE DRAWINGS

In the drawings:

FIG. 1 schematically shows a weight management system 10 according to the invention. The system comprises an input device 11, such as a keyboard, a touch screen, a mouse, a track ball or another type of pointing device for enabling a user to input data concerning food intake events, energy expenditure events and agenda entries. Alternatively, the system 10 may use a microphone and speech recognition software for receiving user input. The user may use the input device 11, for example, for logging when, and what he drinks and eats, what activities he has performed in a certain period, or for entering a time, location and description of appointments and activities he has planned to do in the future. Part of the input data may be received from an electronic agenda, a food intake logging system or an activity logging system. Many known systems and devices for logging or measuring food intake and activities could be used for providing the input. For example, a heart rate measurement device may provide accurate information about the amount of energy a user expends in a given time period. A bike computer may be used for accurately measuring distance and speed for a user traveling by bike. The distance and speed may be used for calculating an amount of expended energy.

Figure 1:
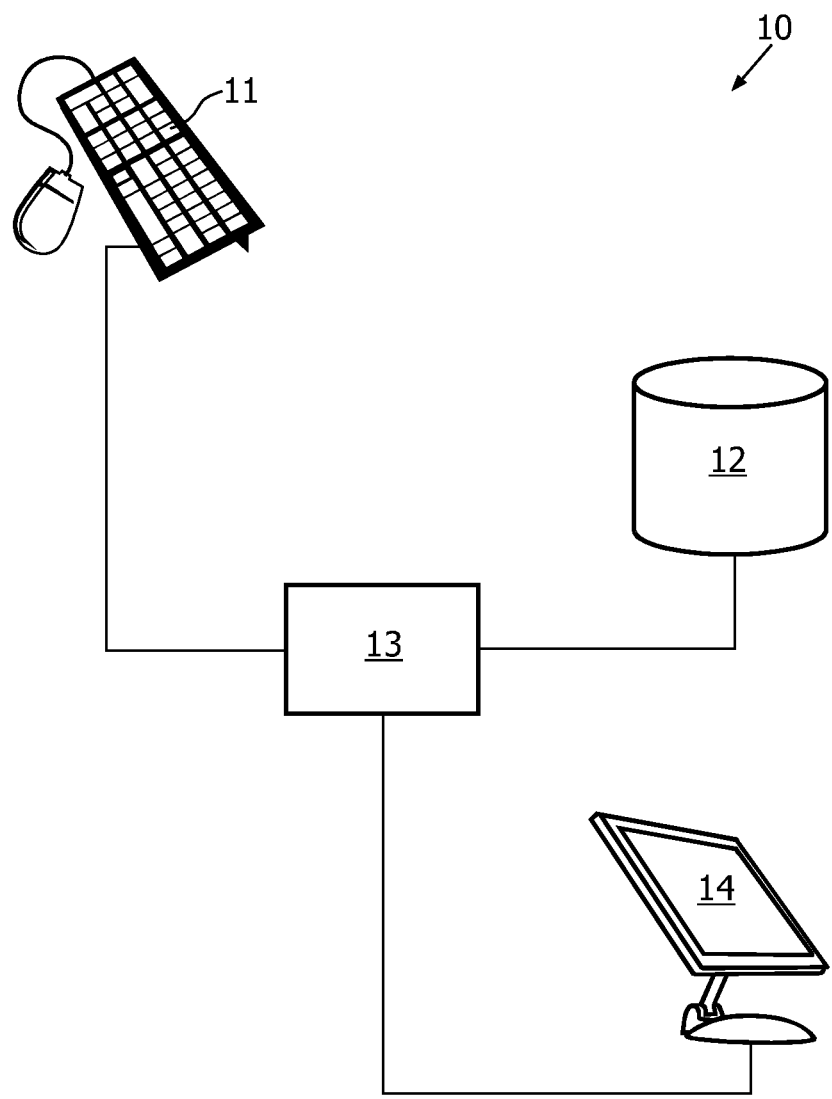
FIG. 1 schematically shows a weight management system according to the invention, FIG. 2, schematically shows a weight management system according to the invention, with a coupling to remote services.

The system 10 further comprises storage means 12 for storing all input data. Optionally, the input data is converted by the processor 13 for enabling storage in a format that is usable for the system. For example, a description of a consumed meal may be converted to a set of nutritional values.

The processor 13 is also operative to send the stored agenda entries to the display 14 or another output device for enabling the user to view the activities he has planned to do. Thereupon, the user may decide to change, add or remove agenda entries, using the input device 11. Electronic agenda's providing the functionality of viewing and editing agenda entries are well known and are often provided as software for a PDA or mobile phone.

According to the current invention, the processor 13 uses the input data to schedule new agenda entries for planning future food intake events and future energy expenditure events. When scheduling the weight-management related items the processor 13 takes the already planned activities on that day into account. The system 10 may, for example, plan eating pasta before heavy exercise, or plan a smaller than usual breakfast when a big lunch meeting is scheduled.

Optionally, when planning food intake events, the system 10 takes the time to buy and prepare dinner into account, and checks whether there is sufficient time to do so. The activity of doing the shopping may be separated in time from the activities of preparing and eating. On busy days, the system 10 may propose simple recipes or healthy take-away dinners. In the event that the user already has the required ingredients at home, or decides to eat at another time, he may edit, add or remove the agenda entries relating to the food intake event.

The food that is selected by the system 10 is selected based on the input data. The system 10 compares the logged food intake of the user to the logged energy expending events. Preferably the system 10 also uses a user profile in which preferences of the user are stored. To a user who exercises a lot and has no weight problems, most suggestions will mainly be based on the preferences. Overweight users will generally be suggested to eat healthy food, which is low on calories. Preferably, amounts of received and expended metabolic energy are monitored and the processor 13 schedules the future food intake events and the future energy expenditure events in such a way as to balance a difference between the received and the expended metabolic energy. This will allow the system 10 to control the user's weight. When a user wants to stabilize his/hers weight, the difference should be approximately zero. When a user wants to lose weight, slightly more metabolic energy should be expended than received.

Alternatively, the received metabolic energy and a user's weight are monitored and the expended metabolic energy is calculated there from, using a model that simulates changes in body composition as a result of energy intake and expenditure. Similarly, the received metabolic energy may be calculated from the expended metabolic energy and the user's weight. However, accurately measuring the expended energy is somewhat more difficult than accurately measuring food intake and user weight.

The scheduled activities are also influenced by other agenda entries. Activity planning may take into account that a user needs relax hours. The system 10 may avoid planning heavy exercise late at night if a user has to wake up very early next morning. Before a business meeting, the system does not plan heavy exercise (e.g. cycling trip), since the resulting sweat could give a bad impression. The system may detect special periods that may induce change into the weight management process. As the last week of the year is well known as a week with lots of food and little exercise, the system 10 may plan less food and more activities in the weeks just before and after this period.

Known food intake logging and activity logging systems may be used for logging the relevant events. Optionally, the events which are planned by the system 10 are automatically logged when the time on which they are planned has come. The user may correct the logged event if he has not, or not exactly, acted in accordance with the plan. Based on past entries, the system learns user preferences in activities and food, and extracts patterns. These preferences can be used as suggestions in future planning. In this way, the user does not have to manually plan these activities.

Preferably, the system takes the user's activity limitations and disabilities into account. To this end, the system 10 enables the user to enter disabilities, or learns the limitations automatically. For example, if a user has a bad knee the system should not suggest long walks.

Figure 2:
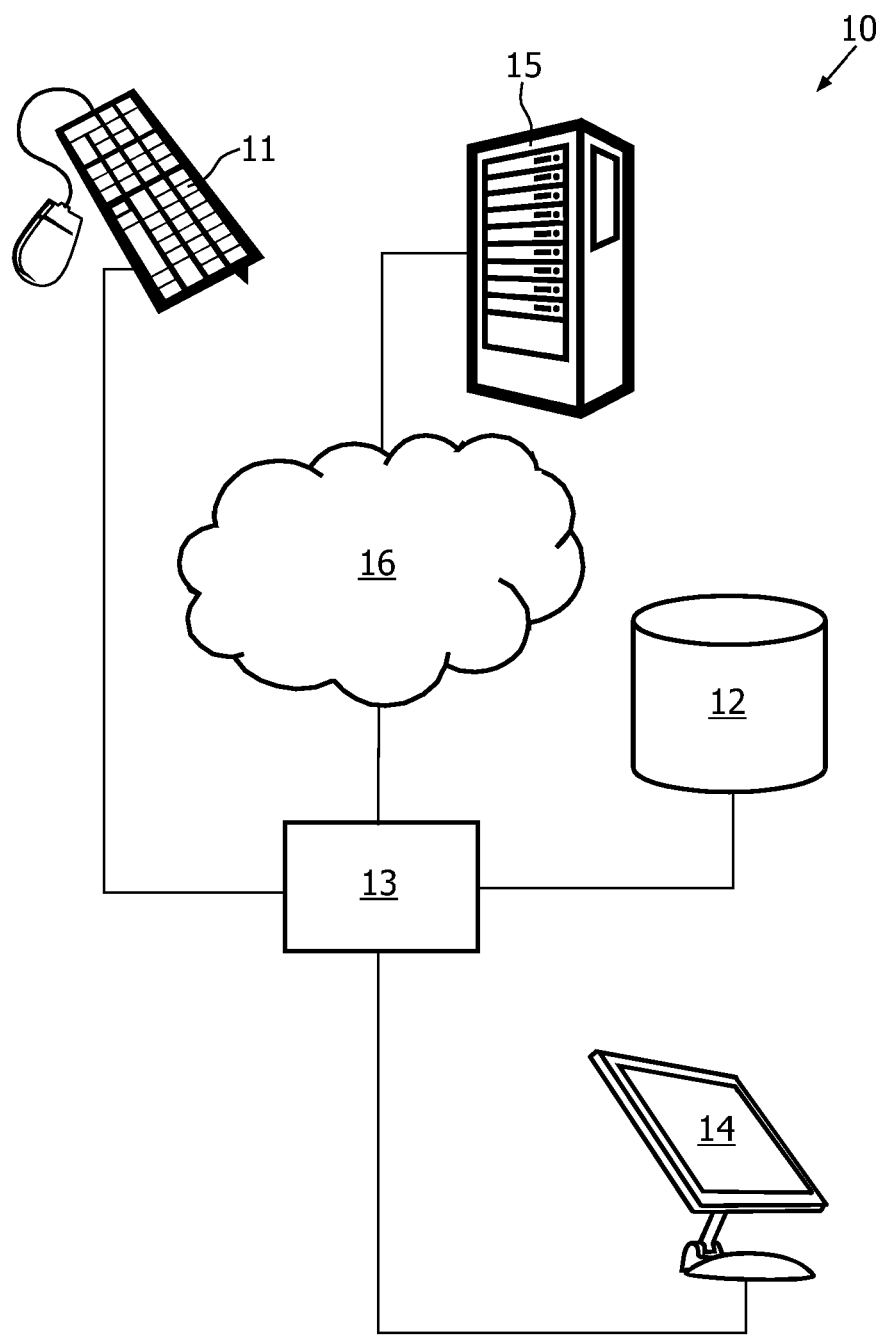

FIG. 2, schematically shows a weight management system 10 according to the invention, with a coupling 16 to remote services 15. The coupling 16 may be realized wired or wireless via, e.g., Bluetooth, GSM, WAP, USB, ADSL, infrared, and/or Internet. The remote services 15 may, for example, provide software updates or additional weight management or agenda related services. A remote server may comprise a large database with information on food intake events and energy expenditure events, which information may be used for logging these events or for further processing of the logged events.

An example of such a remote service 15 is a travel planner, like provided on the Internet at http://journeyplanner.tfl.gov.uk. Such travel planners can recommend routes from one location to another, using, e.g. public transport, walking and/ or cycling and calculate an expected amount of time, needed for the trip. According to an aspect of the invention, two successive agenda entries comprise a location where the event of the agenda entry will occur. The respective locations are sent to a central travel-planning server, which returns information about the recommended route. The information about the recommended route may comprise departure and arrival times, means of conveyance, line numbers of buses, names of subway station, prices of train tickets and much more. Preferably a mix of different means of conveyance is suggested for optimizing time, distance or costs of the trip.

According to the invention, the route is also optimized for weight management and agenda planning. For weight management the amount of energy expended during following a planned route is important. Walking or cycling costs more energy than going by bus and will therefore, in general, be healthier. However, circumstances may occur, which make it more preferable to take a bus or go by car. For example, walking or cycling may take more time than available between the two successive agenda entries. Walking or cycling may cost too much energy, if some other physical exercise has already been planned on the same day. Some distances may be too long for a person. The maximum walking and cycling distance is, preferably, user specific. The system may take physical limitations into account. Via contact with an online weather service, it may be known that there is a high probability of rain at the time of travel, which makes it unpleasant to walk or cycle. In a preferred embodiment, the average walking or cycling speed is used to estimate the transition times from place to place. These average speeds may, for example, be provided by a user or obtained from a GPS unit or bike computer.

In an alternative embodiment, the travel planner may be part of the device that also comprises the processor 13, but that would require a large storage capacity for storing all information, needed for the travel planner. Such an embodiment would preferably still have some connection to an external service for updating the information whereon the travel advice is based.

In Table 1 an exemplary presentation of agenda entries for one day is shown. The table comprises agenda entries provided by the user as well as agenda entries generated by the system. The system has selected the car for going to work in the morning, because of a meeting at a conference center that is too far away from the office to reach by bike. At 13.00, the system has planned a short walk, in order to balance the energy consumption with the energy expenditure for that day. The net energy intake (intake—expenditure) for a day does not have to be 0 every day. The system can also try to balance the energy intake and expenditure over longer periods. For overweight persons, the net energy intake over a longer period should be negative.

TABLE 1

| system generated | start | end | description | energy |
|---|---|---|---|---|
| yes | 7.00 | 7.30 | breakfast | +200 |
| yes | 8.00 | 8.20 | car to work | 0 |
| no | 11.00 | 13.00 | meeting at work | 0 |
| no | 11.45 | 12.15 | lunch | +200 |
| yes | 13.00 | 13.15 | short walk | −100 |
| yes | 14.45 | 15.30 | car to conference center | 0 |
| no | 15.30 | 17.00 | meeting at conference center | 0 |
| yes | 17.00 | 17.50 | car home | 0 |
| yes | 18.30 | 19.30 | dinner | +500 |
| yes | 19.15 | 19.30 | bike to basketball | −100 |
| no | 19.45 | 21.15 | basketball | −600 |
| yes | 21.30 | 21.45 | bike home | −100 |
| | | | TOTAL | 0 |

Figure 3:
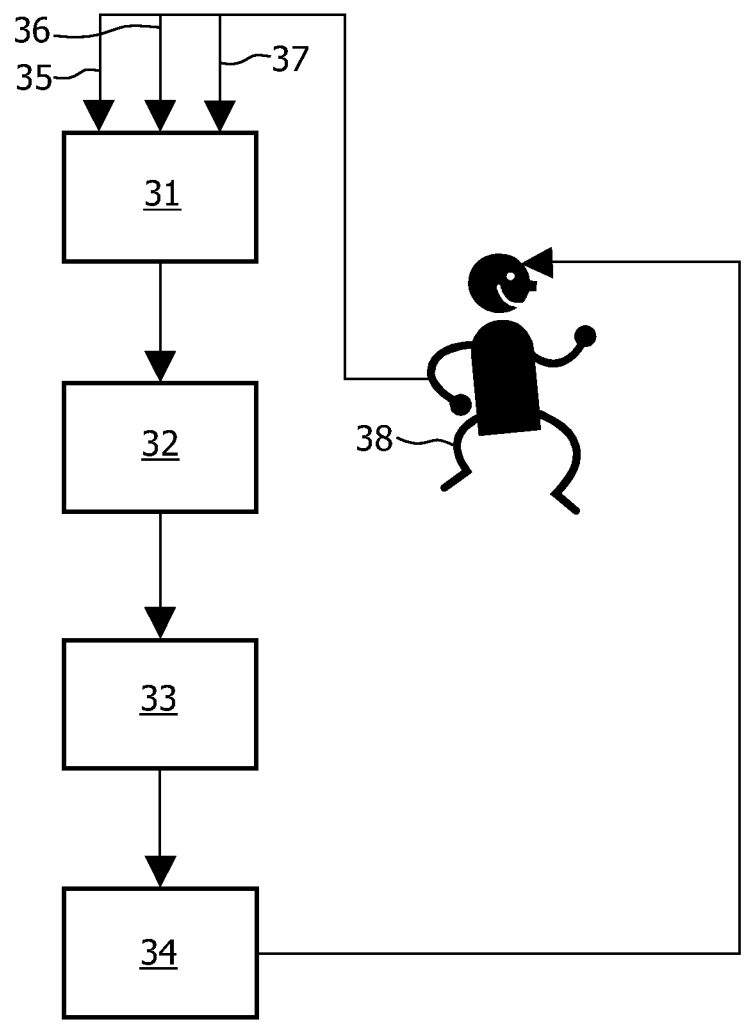
FIG. 3 shows a flow diagram of a method according to the invention.

FIG. 3 shows a flow diagram of a method according to the invention. The method comprises an input step 31 for storing past food intake events 35, past energy expenditure events 36 and agenda entries 37. The input may be received via one or more user interfaces or via, e.g., food logging devices, electronic agenda's, heart rate monitors or bike computers. Then in a scheduling step 32 at least one future food intake event or at least one future energy expenditure event is scheduled, based on the input received at the input step 31. As described above with respect to the system according to the invention, the future food intake and energy expenditure events are placed in a user's normal agenda. The integration of a weight management system and a user's normal agenda results in food intake and energy expenditure advice that can easily be followed without interfering too much in someone's other activities. When a travel planner as described above is also used for the scheduling of the future events, then it might even be possible to live a healthy life without losing much leisure time to exercising. After the scheduling 32, a step of storing 33 the at least one future food intake event or the at least one future energy expenditure event as one of the agenda entries is performed. Then, in a presentation step 34 the agenda entries are presented to the user 83. The presentation is preferably realized, using a display. The user 38 may then follow or not follow the advice and provide information about his or hers actual behavior to the system again in input step 31.

Figure 4:
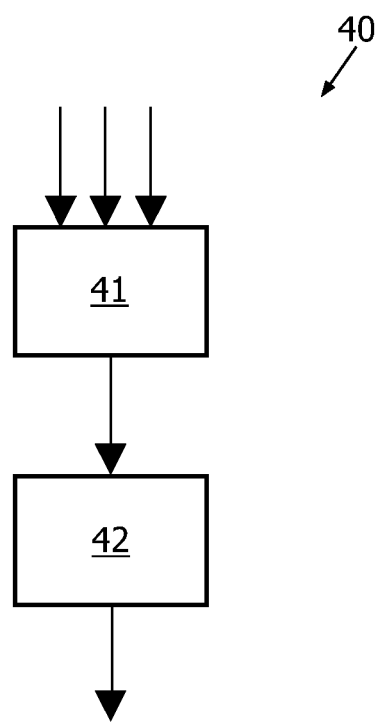
FIG. 4 shows a block diagram of a travel planner according to the invention.

FIG. 4 shows a block diagram of a travel planner 40 according to the invention. The invention comprises an input module 41 for receiving food intake information and/or energy expenditure information and two geographical locations. The food intake information may, e.g., comprise an amount of calories consumed during the last week. The energy expenditure information may, e.g., comprise an amount of calories expended during the last week. The information may also comprise logged food intake or energy expenditure events. The travel planner 40 further comprises a module for generating a travel advice for traveling between the geographical locations, the travel advice comprising at least one tip on a means of conveyance to be used. The tip on the means of conveyance to be used is determined based on the received food intake information and/or energy expenditure information and the two geographical locations. In general, the probability of walking or cycling being advised is larger when the distance between the two locations is smaller and for persons who consume more calories than they expend. Table 2 shows a table with information that may be used by the travel planner 40 to choose which means of conveyance to recommend. It is to be noted that many other information may be taken into account when selecting a means of conveyance.

TABLE 2

| means | average speed | energy expenditure per mile |
|---|---|---|
| walking | ** | *** |
| walking uphill | * | ***** |
| walking downhill | ** | *** |
| walking fast | *** | ***** |
| cycling | **** | *** |
| cycling uphill | *** | ****** |
| cycling downhill | ***** | * |
| cycling fast | ***** | ***** |
| bus | (use bus schedule) | 0 |
| car in city | ******** | * |
| car on highway | ************** | * |
| train | (use train schedule) | 0 |

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A weight management system comprising:
   an input device which logs a user's caloric intake goal, past food intake events and past energy expenditure events and receives agenda entries, the agenda entries each including times and geographical locations;
   a memory which stores the caloric intake goal, the past food intake events, the past energy expenditure events, the agenda entries, and modes of transportation with associated levels of caloric consumption;
   a processor which:
      schedules at least one future food intake event and at least one future energy expenditure event based on the past food intake events, the past energy expenditure events, and the agenda entries,
      adds the future food intake event and the at least one future energy expenditure event to the memory as one of the agenda entries,
      determines one or more possible modes of transportation based on agenda entry times and geographical locations which the user would be able to employ to travel between agenda entry geographical locations within the agenda entry tunes such that the user would he able to employ the one or more possible modes of transportation to travel a distance within a time difference between a current agenda entry nine and geographical location and a next agenda entry time and geographical location
      for each of the one or more possible modes of transportation, determines a level of caloric consumption to travel from each agenda entry geographical location to a next agenda entry geographical location,
      selects one of the possible modes of transportation for traveling to each agenda entry geographical location which most closely balances past and future food intake with the past energy expenditure events and the determined levels of calorie consumption to travel between the agenda entry geographical locations according to the user's caloric intake goal, and
      generates navel advice for travelling between the graphical in dons of successive agenda entries, the travel advice including the selected mode of transportation; and
   display for displaying the agenda entries and the travel advice.

2. The weight management system as claimed in claim 1, wherein
   the input device logs an amount of received metabolic energy and an amount et expended metabolic energy; and
   the processor schedules the at least one future food intake event and the at least one future energy expenditure event, in such a way as to balance a difference between the received and the expended metabolic energy according to the predetermined balancing criterion.

3. The weight management system as claimed in claim 1, wherein the processor determines the mode of transportation to be used based on:
   a distance between the input geographical locations,
   on an amount of available time between the successive agenda entries, and
   on an amount of calorie consumption used in the determined mode of transportation.

4. The weight management system as claimed in claim 1, wherein the mode of transportation includes at least two of walking, running, bicycling, automobile, and public transportation.

5. The weight management system as claimed in claim 1, wherein the processor further determines routing information based on the past and future food intake events and the past and futures energy expenditure events.

6. The weight management system as claimed in claim 1, wherein the predetermined balancing criteria includes at least one of a weight loss criteria and a weight stabilization criteria.

7. A method of managing weight, comprising:
   with a processor, controlling a computer memory to store past food intake events, past energy expenditure events, agenda entries, the agenda entries including times and geographical locations and modes of transportation with associated caloric consumption;

with the processor, scheduling at least one future food intake event and at least one future energy expenditure event, based on the past food intake events, the past energy expenditure events and the agenda entries;

with the processor, cent Ping the computer memory to store the at least one future food intake event and the at least one future energy expenditure event as one of the agenda entries;

in the processor, implementing an algorithm which determines one or more modes of transportation for travelling between the geographical locations of the agenda entries based on the past and/or future food intake events within a time difference between a current agenda entry time and a next agenda entry time, the past and/or future energy expenditure events and the times and geographic locations of the agenda entries in such a way as to balance the caloric consumption and caloric intake between the past and future food intake events, the past and future energy expenditure events, and the times and geographical locations of the agenda entries, according to a predetermined balancing criterion;

in the processor, implementing an algorithm which selects a mode of transposition from the determined one or more modes of transportation, the selected mode of transportation having the balance closest to the predetermined balancing criterion, and with the processor, at least one of controlling a display device to display the agenda entries and the selected mode of transportation and the computer memory to store the selected mode of transportation.

8. The method according to claim 7, wherein the past food intake events comprise an amount of received metabolic energy and the past energy expenditure events comprise an amount of expended metabolic energy.

9. The method according to claim 8, wherein the at least one future food intake event and the at least one future energy expenditure event is scheduled such that the received and the expended metabolic energy balance according to the predetermined balancing criterion.

10. The method according to claim 7, wherein the mode of transportation includes at least two of walking, running, bicycling, automobile, and public transportation.

11. The method according to claim 7, further including:
with the processor, determining routing information based on the past and future food intake and the past and future energy expenditure events.

12. A non-transitory computer readable storage medium carrying instructions which control a processor to carry out a computer executed method of weight management, the computer executed method comprising
controlling a computer memory to store past food intake events, past energy expenditure events, agenda entries, the agenda entries including times and geographical locations and modes of transportation with associated caloric consumption;
scheduling at least one future food intake event and at least one future energy expenditure event, based on the past food intake events, the past energy expenditure events and the agenda entries;
controlling the computer memory to store the at least one future feed intake event and the at least one future energy expenditure event as one of the agenda entries;
determining one or more modes of transportation for travelling between the geographical locations of the agenda entries based on the past and/or future fund intake events within a time difference between a current agenda entry time and a next agenda entry time, the past and/or future energy expenditure events and the times and geographic locations of the agenda entries in such is way as to balance the caloric consumption and caloric intake between the past and future hind intake events, the past and future energy expenditure events, and the times and geographical locations of the agenda entries;
selecting a mode of transportation from the one or more determined modes of transportation having the difference closest to a users caloric balancing criterion, and
at least one of controlling a display device to display the agenda entries and the selected mode of transportation and the computer memory to store the selected mode of transportation in a memory.

13. A method of managing weight, comprising;
(a) entering into a computer at time period;
(b) entering into the computer to user's calorie goal, wherein the goal is a number not calories the user desires to consume within the time period;
(c) entering into the computer a total caloric intake for the time period;
(d) entering into the computer a plurality of appointments for the user during the time period, wherein each appointment specifies a location and a time by which the use must be at the location;
(e) sorting, with the computer, the plurality of appointments into chronological order;
(f) storing in the computer a plurality of modes of transportation, wherein each mode of transportation is associated with a speed and a level of caloric consumption;
(g) for each appointment except for the last appointment of the tune periods;
  (i) determining, with the computer, the distance between the current appointment location and the next chronological appointment location;
  (ii) determining, with the computer, the time difference between the current appointment location and the next chronological appointment location;
  (iii) determining, with the computer, one or more possible modes of transportation based on the distance and the time difference to the next Chronological appointment location such that the user would be able to employ the one or more possible modes of transportation to travel the distance within the time difference;
  (iv) for each one or more possible modes of transportation, determining, with the computer, the difference between the associated level of caloric consumption and the total caloric intake for the time period;
  (v) sorting the one or more possible modes of transportation based on the difference calculated in step (g)(iv);
  (vi) selecting, with the computer, a mode of transportation from the one or more possible modes of transportation, wherein the selected mode of transportation has the difference closest to the user's calorie goal;
(h) displaying the plurality of selected suggested modes of transportation and the associated appointment to the user.

14. The method according to claim 13, wherein the modes of transportation includes at least two of walking, running, bicycling, automobile, aid public transportation.

15. The method according to claim 13, further including:
with the computer, determining routing information between the at least two input geographic locations optimized for weight management and appointment planning.

* * * * *